United States Patent
Serban et al.

(10) Patent No.: US 8,609,427 B2
(45) Date of Patent: *Dec. 17, 2013

(54) SO2 DETECTION USING DIFFERENTIAL NANO-RESONATORS AND METHODS RELATED THERETO

(75) Inventors: Bogdan Catalin Serban, Bucharest (RO); Cornel P. Cobianu, Bucharest (RO); Mihai N. Mihaila, Bucharest (RO); Viorel Georgel Dumitru, Prahova (RO)

(73) Assignee: Honeywell Romania s.r.l., Bucharest (RO)

( * ) Notice: Subject to any disclaimer, the term of this patent is extended or adjusted under 35 U.S.C. 154(b) by 365 days.

This patent is subject to a terminal disclaimer.

(21) Appl. No.: 12/962,301

(22) Filed: Dec. 7, 2010

(65) Prior Publication Data

US 2011/0143448 A1 Jun. 16, 2011

(30) Foreign Application Priority Data

Dec. 11, 2009 (EP) ..................................... 09178794

(51) Int. Cl.
*G01N 33/00* (2006.01)
*G01N 29/036* (2006.01)
*G01N 29/32* (2006.01)
*G01N 29/44* (2006.01)

(52) U.S. Cl.
USPC .... 436/122; 73/24.06; 422/82.01; 422/82.02; 422/82.03; 422/82.04; 422/83; 422/88; 422/98; 436/119

(58) Field of Classification Search
USPC .......... 422/82.01–82.04, 83, 88, 98; 436/119, 436/122; 73/24.06
See application file for complete search history.

(56) References Cited

U.S. PATENT DOCUMENTS

| | | | | | |
|---|---|---|---|---|---|
| 3,437,446 | A | * | 4/1969 | Pierce | 436/116 |
| 3,744,296 | A | * | 7/1973 | Beltzer | 436/142 |
| 4,111,036 | A | * | 9/1978 | Frechette et al. | 73/24.06 |
| 4,759,210 | A | * | 7/1988 | Wohltjen | 73/31.07 |

(Continued)

FOREIGN PATENT DOCUMENTS

| WO | WO-9713143 A1 | 4/1997 |
|---|---|---|
| WO | WO-0066266 A1 | 11/2000 |
| WO | WO-2008088867 A1 | 7/2008 |

OTHER PUBLICATIONS

Fuest, R. W. et al, Technical Report Nov. 1968, 51 pages.*

(Continued)

*Primary Examiner* — Arlen Soderquist
(74) *Attorney, Agent, or Firm* — Schwegman, Lundberg & Woessner, P.A.

(57) ABSTRACT

A sulfur dioxide sensor comprising a first beam having a functionalized sensing surface capable of sensing sulfur dioxide, the first beam capable of producing a first resonant frequency; and a second beam having a functionalized reference surface not capable of sensing sulfur dioxide, the second beam capable of producing a second resonant frequency, wherein differential sensing of sulfur dioxide may be performed, further wherein the first beam is functionalized with a liquid phase of a first polymeric compound and the second beam is functionalized with a liquid phase of a second polymeric compound is provided. In one embodiment, the sensor is a nano-sensor capable of low drift accurately detecting sulfur dioxide levels at the zeptograms level. Methods of making and using a sulfur dioxide sensor are also provided.

20 Claims, 2 Drawing Sheets

(56) References Cited

U.S. PATENT DOCUMENTS

| | | | |
|---|---|---|---|
| 5,296,374 A * | 3/1994 | Culshaw et al. | 435/287.9 |
| 6,432,362 B1 * | 8/2002 | Shinar et al. | 422/82.01 |
| 6,523,392 B2 * | 2/2003 | Porter et al. | 73/24.01 |
| 6,575,020 B1 * | 6/2003 | de Charmoy Grey et al. | 73/54.23 |
| 7,052,854 B2 * | 5/2006 | Melker et al. | 435/7.1 |
| 7,935,191 B2 * | 5/2011 | Mutharasan et al. | 134/1 |
| 8,268,630 B2 * | 9/2012 | Fedder et al. | 436/149 |
| 2004/0223884 A1 * | 11/2004 | Chen et al. | 422/88 |
| 2006/0177349 A1 * | 8/2006 | Thaysen et al. | 422/82.02 |
| 2006/0198760 A1 * | 9/2006 | Potyrailo et al. | 422/82.01 |
| 2007/0059212 A1 * | 3/2007 | Masters et al. | 422/88 |
| 2008/0069732 A1 * | 3/2008 | Yi et al. | 422/82.01 |
| 2009/0011946 A1 * | 1/2009 | Majumdar et al. | 506/9 |
| 2010/0022731 A1 * | 1/2010 | Ryan et al. | 526/263 |
| 2010/0203648 A1 * | 8/2010 | Porter et al. | 436/109 |
| 2011/0113856 A1 | 5/2011 | Cobianu et al. | |
| 2011/0129929 A1 * | 6/2011 | Day et al. | 436/8 |

OTHER PUBLICATIONS

Janghorbani, M. et al, Analytical Chemistry 1973, 45, 325-332.*
Hashida, I. et al, Nippon Kagaku Kaishi 1973, 1195-1200.*
Frechette, M. W. et al, Analytical Chemistry 1973, 45, 1765-1766.*
Harrison, J. W. et al, Technical Report EPA-2-76-034 Feb. 1976, 194 pages.*
Ranucci, E. et al, Mikrochimica Acta 1995, 120, 257-270.*
Ferrari, V. et al, Sensors and Actuators B 2000, 68, 81-87.*
Matsuguchi, M. et al, Sensors and Actuators B 2001, 77, 363-367.*
Shi, G. et al, Talanta 2001, 55, 241-247.*
Agbor, N. E, et al., "Polyaniline thin films for gas sensing", Sensors and Actuators B: Chemical, 28(3), (Sep. 1995), 173-179.
Arntz, Y., et al., ""Label-free protein assay based on a nanomechanical cantilever array"", (Dec. 20, 2002), 86-90 pgs.
Benmakroha, Farida, et al., "Monitoring of sulfur dioxide using a piezoelectric crystal based controller", Analyst, 18(4), (Apr. 1993), 401-406.
Endres, H. E, et al., "Impedance spectroscopy on dielectric gas sensors", Sensors and Actuators B: Chemical, 22(1), (Oct. 1994), 7-11.
Gfeller, K. Y, et al., ""Micromechanical oscillators as rapid biosensor for the detection of active growth of *Escherichia coli*"", vol. 21(3), Biosensors and Bioelectronic, Elsevier BV, NL LNKD- DOI:10.1016/J.81OS.2004.11.018,, (Sep. 15, 2005), 528-533.
Leidl, Anton, et al., "A new SO2 sensor system with SAW and IDC elements", Sensors and Actuators B: Chemical, 34(1-3), (Aug. 1996), 339-342.
Pribil, R., et al., "The use of a piezoelectric crystal to determine sulphur dioxide in gases", Talanta, 39(4), (Apr. 1992), 361-6.
Ranucci, Elisabetta, et al., "Use of poly(amidoamines) as CO2- and Si2-sensitive material for gravimetric sensors", Microchimica Acta, 120(1-4), (Mar. 1995), 257-270.

* cited by examiner

SO2 DETECTION USING DIFFERENTIAL NANO-RESONATORS AND METHODS RELATED THERETO

RELATED MATTERS

This application claims priority under 35 USC §119 to European Application Serial Number 09 178794.5, filed Dec. 11, 2009, which is incorporated herein by reference in its entirety.

BACKGROUND

Ambient air naturally contains sulfur dioxide (SO2) at a Threshold Limit Value (TLV) of two (2) parts per million (ppm). In large amounts, sulfur dioxide (SO2) is considered a highly toxic air pollutant. SO2 can be emitted by volcanoes in large amounts, and as a result of activities such as combustion of fossil fuels (e.g., coal and petroleum), power plant emissions, during oxidation of organic compounds, and the like. Further oxidation of SO2 produces acid rains, which negatively impact eco-systems. Increasingly stringent regulations are directed to a reduction of permissible levels of SO2 in ambient air. Current National Ambient Air Quality Standards (NAAQS) require annual arithmetic values of SO2 to be smaller than 30 ppb.

SUMMARY

The inventors recognize the need for providing gas sensing devices with reduced drift, improved accuracy and high sensitivity. Additionally, the inventors recognize the need for providing gas sensing devices which can accurately detect $SO_2$ emissions in ranges smaller than parts per million (ppm) in the ambient air. The novel sensors described herein provide improved accuracy together with the ability to detect ultra small gas concentrations on the order of parts per billion (ppb), parts per trillion (ppt) or smaller. In other embodiments, the devices may be used in micro-scale electromechanical systems.

A sulfur dioxide sensor comprising a first beam having a functionalized sensing surface capable of sensing sulfur dioxide, the first beam capable of producing a first resonant frequency; and a second beam having a functionalized reference surface not capable of sensing sulfur dioxide, the second beam capable of producing a second resonant frequency, wherein differential sensing of sulfur dioxide may be performed is provided. In one embodiment, the sensor is a nanosensor capable of accurately detecting sulfur dioxide levels at the zeptogram level. In one embodiment, the sensor has low drift, as compared to conventional differential resonant sensors, which use bare surfaces on the second beam. In general, a "low drift" sensor refers to a sensor with a baseline drift which is at least five times lower than the sensor resolution itself, thus allowing the sensor to preserve its accuracy within its entire dynamic range, for its entire sensor lifetime. In one embodiment, the functionalized sensing surface and the functionalized reference surface are each ultra thin.

In one embodiment, the functionalized sensing surface is functionalized using a first polymeric compound, including, but not limited to poly(2-vinylpyridine), poly(4-vinylpyridine), poly(4-vinylpyridine-co butylmethacrylate), and combinations thereof. In one embodiment, the functionalized reference surface is functionalized using a second polymeric In one embodiment, the sensor is a resonant nanosensor capable of performing differential sensing by monitoring changes in the resonant frequency of the first beam relative to the resonant frequency of the second beam. The first and second beams of the sensor may be located on a single silicon substrate or on different silicon substrates.

In one embodiment, the sensor further comprises a first frequency measuring circuit for measuring the resonant frequency of the first beam; a second frequency measuring circuit for measuring the resonant frequency of the second beam; and a control for analyzing the signals from the first frequency measuring circuit and the second frequency measuring circuit, wherein a differential frequency equivalent to the first frequency minus the second frequency is determinable, wherein differential sensing of sulfur dioxide exposure is performed.

Embodiments of the invention further comprise a method of forming a sulfur dioxide sensor comprising functionalizing a first silicon surface with a liquid phase of first polymeric compound, which is further thermally treated in order to become a solid state ultrathin sensing film (e.g., between about three (3) up to no more than about five (5) nanometers (nm) in thickness, although portions of the film may exceed five (5) nm), used to detect $SO_2$; and functionalizing a silicon surface with a liquid phase of a second polymeric compound, which is further thermally treated in order to become a solid state ultrathin reference film able to prevent detection of $SO_2$. In one embodiment, the liquid phase of the first polymeric compound is obtained by dissolution in pyridine. In one embodiment, the liquid phase of the second polymeric compound is obtained by dissolution in ethanol.

Embodiments of the invention further comprise a method of detecting sulfur dioxide comprising exposing first and second beams to sulfur dioxide, wherein the first beam has a functionalized surface to detect sulfur dioxide and the second beam has a functionalized surface functionalized to prevent detection of sulfur dioxide; and comparing the resonant frequency of the first beam to the resonant frequency of second beam, wherein an amount of sulfur dioxide exposure is determined.

In one embodiment, the invention further comprises connecting frequency measuring circuit to the functionalized silicon surface of a suspended vibrating beam (e.g., clamped-clamped silicon beam, as a portion of a silicon chip) to produce differential resonant frequency changes; connecting a mixer to the output of the frequency measuring circuits in order to measure the differential resonant frequency changes; and outputting the differential resonant frequency changes to a presentation device.

Embodiments of the invention further comprise a method of detecting sulfur dioxide comprising exposing first and second beams to sulfur dioxide, wherein the first beam has a functionalized surface to detect sulfur dioxide and the second beam has a functionalized surface to prevent detection of sulfur dioxide; and comparing the resonant frequency of the first beam to the resonant frequency of second beam, wherein an amount of sulfur dioxide exposure is determined. In one embodiment, the first and second beams are nano-beams.

Embodiments of the novel $SO_2$ gas sensors described herein are low in cost and high performance with drift free and excellent mass resolution. In one embodiment, resonant differential principles are applied to silicon nano-electromechanical systems (NEMS), thus allowing for detection in the range of hundreds of zeptograms of $SO_2$, with baseline drift elimination.

DETAILED DESCRIPTION

Figure 1:
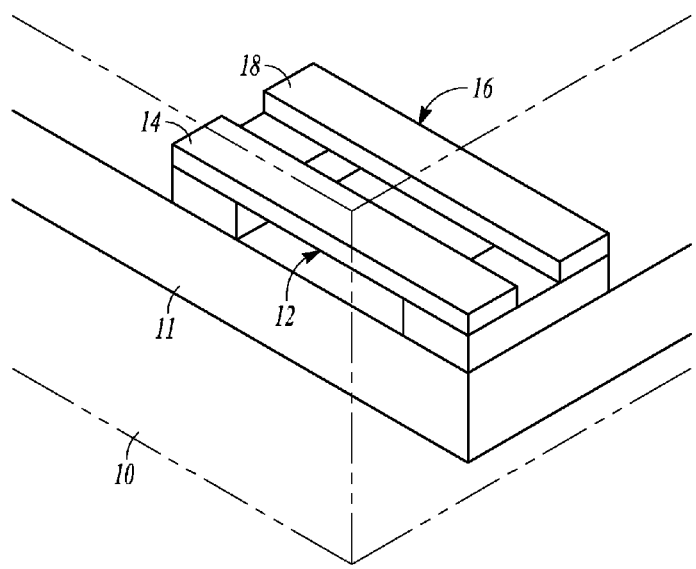
FIG. 1 is a simplified illustration of a sulfur dioxide ($SO_2$) resonator according to an example embodiment.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, chemical and procedural changes may be made without departing from the scope of the present invention. The following description of example embodiments is, therefore, not to be taken in a limited sense, and the scope of the present invention is defined by the appended claims.

The Detailed Description that follows begins with a brief overview of conventional differential sensing devices, a description of the embodiments and a brief conclusion.
Conventional Differential Bio-Chemical Sensing Devices Conventional differential bio-chemical sensing devices based on the resonance principle may include a resonant sensing loop, a resonant reference loop and an electronic mixer which outputs the difference between the resonance frequencies provided by each of the sensing and reference loops. Both loops comprise an identical electronic readout circuit for frequency measurement and a circuit to determine the resonance frequency. The resonant sensing loop comprises a "vibrating" device exposed to the external environment to be monitored, i.e. a bio-chemical resonant sensor having a functionalized surface or a sensing layer chemically designed to adsorb or absorb and detect the desired bio-chemical component (gas or bio component) by its reversible reaction with the functionalized surface.

The resonant reference loop in these prior art differential bio-chemical resonant sensors comprises a "vibrating" device with the same geometry as the sensor, but having a bare surface or an uncoated surface. As a result, the prior art bare (uncoated) surface is likely to have a different response to external conditions (e.g., humidity in the ambient air, temperature, ageing, and the like) as compared to the sensing layer. Thus, when the resulting signals of the sensing and reference loop are sent through the mixer for comparison, the effect of this external effect, such as humidity, are not eliminated.

Additionally, if the visco-elastic properties of the functionalized sensing layer are changing over time, the resonance frequency of the sensing loop is influenced. Therefore, in the prior art, when making the frequency subtraction, these ageing influences cannot be subtracted from the mixer's response, as these effects are not present in the uncoated reference device.

Therefore, the "common mode signals" such as humidity, ageing of the sensing layer, and the like, cannot be eliminated at the mixer level, as they are not present in both terms to be subtracted. Such influences, i.e., susceptibility to external effects, result in a significant amount of "baseline drift," leading to reduced accuracy. Additionally, the prior art sensors are only able to discern gaseous levels in the parts per million (ppm) range.

DESCRIPTION OF THE EMBODIMENTS

In contrast, embodiments of the present invention comprise a bio-chemical differential sensor with a resonant reference loop comprising a functionalized ultra thin reference layer (hereinafter "functionalized reference layer") on the reference beam surface with visco-elastic properties similar to the functionalized ultra thin sensing layer (hereinafter "functionalized sensing layer"), but having been altered (such as with a coating) to produce a functionalized reference beam (hereinafter "functionalized reference beam") having no sensing properties. As used herein, the term "ultra thin" refers to a layer having a thickness of no more than five (5) nanometers (nm), although portions of the layer may have a thickness greater than five (5) nm. Use of ultra thin layers preserves the inertial mass of the beams in use, i.e., during vibration, so that high mass resolution needed for high sensor-sensitivity is further preserved after the corresponding functional layers are deposited on the first and the second beam.

Use of a non-sensing functionalized reference layer in the reference loop allows, for the first time, full scale differential sensing, which is not only highly accurate and drift-free, but capable of discerning $SO_2$ content in extremely small amounts of $SO_2$, such as in the zeptogram range.

FIG. 1 illustrates an example of sulfur dioxide sensor 10. The sulfur dioxide sensor 10 includes a substrate 11 with a first beam 12 and a second beam 16 formed on the substrate 11. Although the first and second beams 12, 16 are shown on the same substrate 11, embodiments are contemplated where the first and second beams 12, 16 could be also on different substrates.

Figure 2:
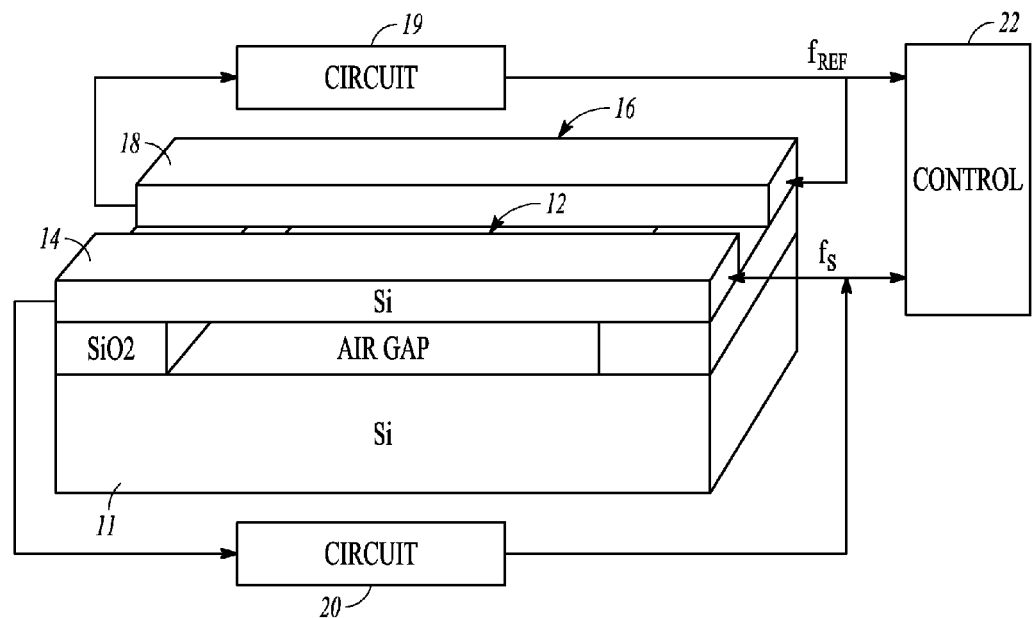
FIG. 2 is an enlarged view illustrating a portion of the $SO_2$ sensor shown in FIG. 1 according to an example embodiment.

FIG. 2 is an enlarged view illustrating a portion of the sulfur dioxide sensor shown in FIG. 1. The first beam 12 includes a first functionalized sensing layer 14 and the second beam 16 includes a second functionalized reference layer 18. Each of the functionalized sensing and reference layers 14 and 18, respectively possess similar visco-elastic properties and ageing properties and will respond similarly to ambient temperature and humidity (e.g., similar hydrophilic or hydrophobic properties).

A "functionalized surface" refers hereinafter to a beam surface modified in a manner to perform a desired function, i.e., to either sense (sensing beam) or to not sense (reference beam), by means of an ultra thin layer deposited on that beam. Embodiments are contemplated in which the first and second sensing and reference functionalized surfaces, 14 and 18, respectively are each functionalized in a different manner to perform the desired function according to any suitable method, such as any one of Schemes 1-4 described herein. The functionalized surfaces 14, 18 may be part of the first and second beams 12, 16, respectively or formed as part of a layer or coatings added to the beams.

In use, the sulfur dioxide sensor 10 performs differential sensing of sulfur dioxide by monitoring changes in the resonant frequency of the first beam 12 relative to the resonant frequency of the second beam 16. Therefore, the sulfur dioxide sensor 10 may further include a first frequency measuring circuit 20 for measuring the resonant frequency of the first beam 12 and a second frequency measuring circuit 19 for measuring the resonant frequency of the second beam 16.

The frequency measuring circuits 19 and 20 may operate, for example, according to the principle of phase lock loop circuits. (See, for example, U.S. Pat. No. 6,722,200, (hereinafter '200), which is hereby incorporated by reference in its entirety). Each of the circuits 19 and 20 provide the resonance frequency of the corresponding beams. In one embodiment, the invention provides an all differential resonant sensor, where the resonance frequencies of the two beams are subtracted at the level of an electronic reader, in order to get a frequency difference which will eliminate the common mode signal due to humidity, ageing, etc, as is discussed in U.S. patent application Ser. No. 12/617,893 entitled, "All-Differential Resonant Nanosensor Apparatus and Method, filed on Nov. 13, 2009 (hereinafter" '893), which is hereby incorporated by reference herein in its entirety.

A differential reading electronic circuit, comprising a mixer with the two frequency signals at the input and with the frequency difference at the output may be interconnected with each resonant beam pair (sensing and reference) for signal processing. By subtracting the frequency response from the sensing loop and the reference loop, a drift-free frequency signal for $SO_2$ may be obtained. If desired, two electronic oscillators may be used for the reading of the two resonance frequencies. In this case, each oscillator is made of an amplifier having in its feed-back loop a vibrating beam.

Figure 3:
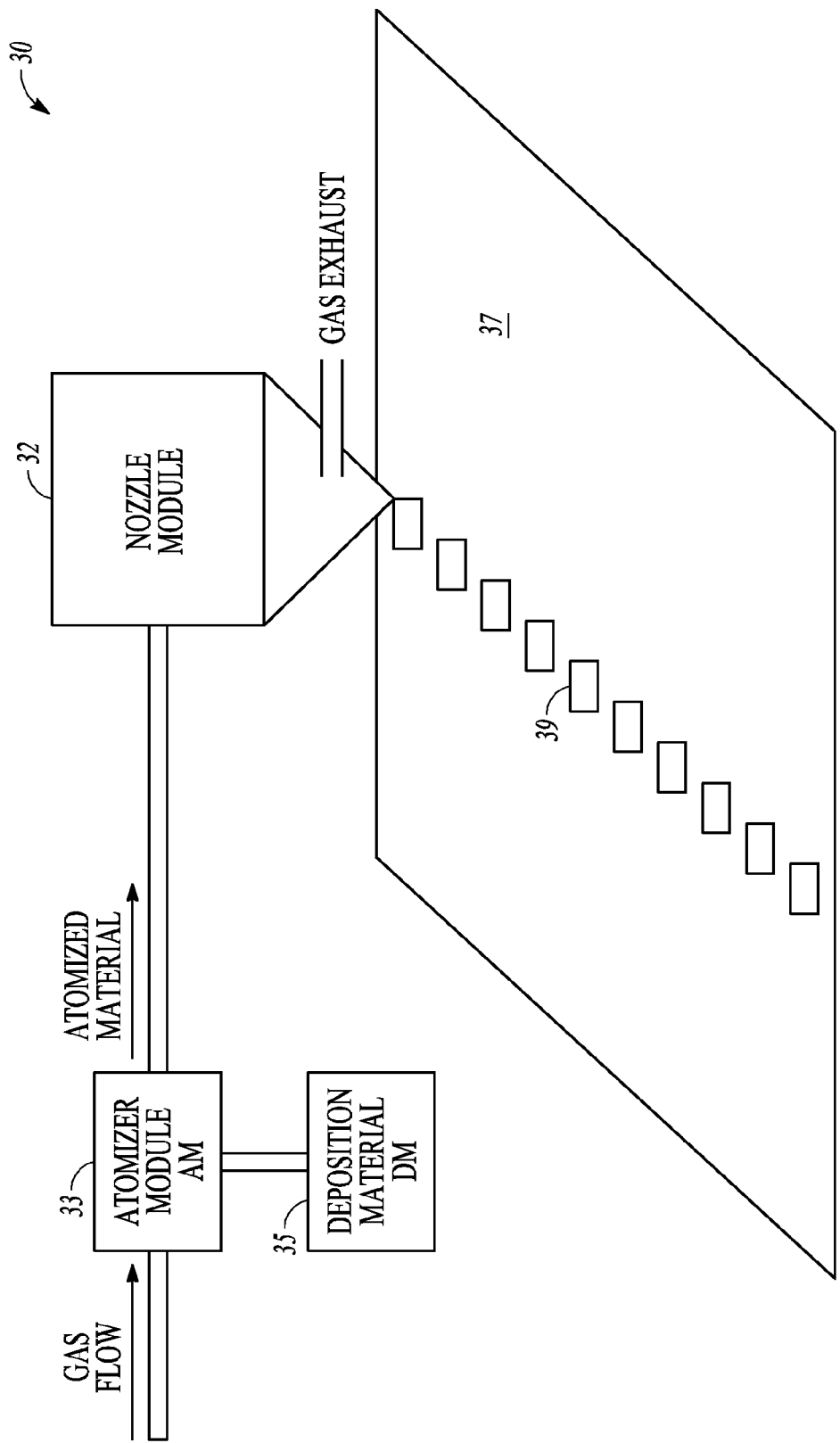
FIG. 3 is a simplified illustration of a dual-head direct printing system for preparing a functionalized surface according to an example embodiment.

The first and second frequency measuring circuits 19, 20 may be a variety of electronic circuits. In one embodiment, the first and second frequency measuring circuits 19, 20 are similar to the circuits disclosed in U.S. Pat. No. 6,722,200, which is hereby incorporated by reference in its entirety. In some embodiments, the first and the second frequency measuring circuits 19, 20 send signals to a mixer or control 22 for differential sensing as described in '893, supra. Specifically, as mentioned above, at the output of the mixer 22, the difference of the frequencies measured by the two frequency measuring circuits 19 and 20. The frequency difference will give a drift free, high accuracy information about the gas to be detected In one embodiment, the devices and methods described herein are compatible with conventional integrated circuit (IC) processing, as this term is understood in the art. FIG. 3 is an illustration of one embodiment of a dual-head direct printing system 30 useful herein. In this system 30, each type of deposition material 35 (DM1) and 41 (DM2), uses its own distribution system for local, selective and additive direct deposition of the desired material. For example, a first print head (NM1) 32 may be supplied with atomized DM1 from a an atomizer module (AM1) 33 connected to a DM1 source 35 and a suitable gas supply, as is known in the art, for deposition of the atomized DM1 on a silicon surface (e.g., wafer) 37 to form a functionalized sensing layer 36 (such as an ultrathin sensing layer) on the silicon wafer 37 as shown. Referring again to FIGS. 1 and 2, the functionalized sensing layer 36 (FIG. 3) may be present on the first beam 12 of all chips located on the substrate 11, such as wafer 37 (FIG. 3).

A second print head (NM2) 38 may be supplied with atomized DM2 from an atomizer module (AM2) 39 connected to a DM2 source 41 and a suitable gas supply, for deposit of the atomized DM2 on the silicon surface 37 to form a functionalized reference layer 42 on the second beam 16 of all chips on a wafer. In this embodiment, the second deposition material 40 (which, after a thermal treatment will become the solid state sensing layer 42) from any reference beam on the wafer comprises a deposition material having similar visco-elastic properties similar to the first deposition material 34, from any sensing beam 12 on a wafer but which instead comprises a material chemically designed to essentially "de-functionalize" the second functionalized sensing surface 42 to produce a non-sensing functionalized reference surface. Direct printing may be considered a type of post-processing performed on a silicon substrate, such as a wafer, prior to subsequent steps, such as packaging and dicing. Through use of selective additives as described herein, there is now no need for post-print etching.

Methods for on-wafer functionalization of an all differential SO2 resonant nano-sensor containing a tandem of a sensing ultra thin polymeric layer which is obtained in the liquid phase by dissolving in a suitable polymeric compound, such as pyridine, and depositing same on the surface of the first (sensing) silicon beam 12. In one embodiment, the polymeric compound is selected from poly(2-vinylpyridine), poly(4-vinylpyridine), poly(4-vinylpyridine-co butylmethacrylate), and combinations thereof. In this embodiment, a polystyrene compound obtained in the liquid phase by dissolving in a suitable alcohol, such as ethanol, and depositing same on the surface of the second non-sensing (reference) silicon beam 16. In this embodiment, both vibrating beams are located on the same chip and being excited to resonance and integrated with identical electronics, although the invention is not so limited. In one embodiment, each of the vibrating beams (sensing and reference) are located on different chips while being excited to resonance and integrated with identical electronics.

In one embodiment, the chemical design of the functional sensing group in the sensing ultra thin layer is based on Pearson's Hard Soft (Lewis) Acid Base (HSAB) principle. According to this theory, a hard Lewis base prefers to bond to a hard Lewis acid, and a soft Lewis base prefers to bond to a soft Lewis acid. Additionally, a borderline base tends to interact with a borderline acid. Thus, since $SO_2$ is a borderline acid, it should have a preference for a borderline base. Borderline bases useful herein include, but are not limited to, aromatic amines, pyridine, azide, bromide and nitrite ions, as well as pyridine units-base polymers as sensitive moiety for SO2 detection.

Multiple chemical routes using sequential steps are possible for providing silicon surface functionalization of both the sensing layer and the reference layer through use of borderline bases on the sensing layer and with a compound not capable of sensing sulfur dioxide, such as polystyrene. The borderline bases are essentially being used as anchors for $SO_2$ sensing.

Appropriate technical approaches are performed for functionalization compatibility with integrated circuit (IC) technology flow for NEMS fabrication as is known in the art. In most embodiments, care is taken to avoid allowing the suspended beam to stick to the substrate. In most embodiments, the processed substrates may be subject to treatments (such as diluted HF) in a gaseous phase rather than a liquid phase, in order to minimize the risk of suspended beam sticking to the substrate.

Various routes to obtain the desired sensors are possible. Four possible routes are shown here. It is understood that all silicon substrates are cleaned prior to being exposed to the various deposition materials to the extent needed as is understood in the art.

Route #1

In this embodiment, at least a portion of a silicon beam, i.e., a "first sensing beam" is functionalized with a poly (2-vinyl pyridine) material:

Sensitive layer:

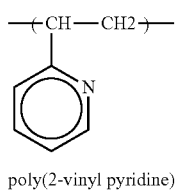

poly(2-vinyl pyridine)

and at least another portion of a silicon beam, i.e., a "second sensing beam" is functionalized with a polystyrene material:

Reference layer:

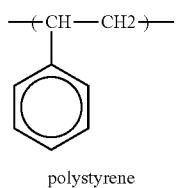

polystyrene

The functionalization may occur simultaneously or sequentially. In one embodiment, as discussed above in FIG. 3, the silicon substrate(s) are functionalized using the desired compound in its liquid phase according to direct printing methods known in the art. Any suitable conditions may be used to achieve the desired function. In one embodiment, the silicon substrate(s) are dried and heated to a temperature and for a period of time sufficient to obtain solid-state films on each surface. In one embodiment, the temperature is at least about 50° C.

Route #2

The same route as described in Route #1 is followed, except that the first sensing beam is functionalized with a poly(4-vinyl pyridine) material:

Sensitive layer:

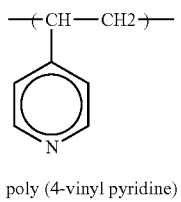

poly (4-vinyl pyridine)

Route #3

The same route as described in Route #1 is followed, except that the first sensing beam is functionalized with a poly(4-vinyl pyridine co-butyl methylacrylate) material:

Sensitive layer:

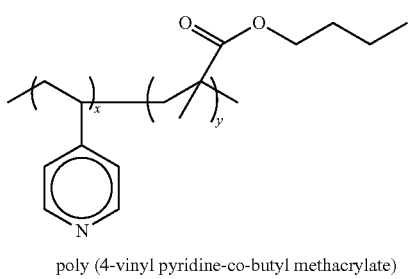

poly (4-vinyl pyridine-co-butyl methacrylate)

Route #4

The same route as described in Route #1 is followed, except that the first sensing beam is functionalized with a poly(2-vinylpyridine co-styrene) material:

Sensitive layer:

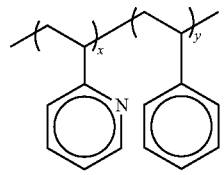

poly (2-vinyl pyridine-co-styrene)

CONCLUSION

A novel a low cost, drift free, high performance $SO_2$ gas sensor is provided which uses resonant differential principles. In one embodiment, this technology is applied to silicon nano-electromechanical systems (NEMS). In one embodiment, a vibrating functionalized nano-beam changes resonance frequency as a function of $SO_2$ gas concentration in the ambient air.

Although specific embodiments have been illustrated and described herein, it will be appreciated by those of ordinary skill in the art that any procedure that is calculated to achieve the same purpose may be substituted for the specific embodiments shown. This application is intended to cover any adaptations or variations of the present subject matter. Therefore, it is manifestly intended that embodiments of this invention be limited only by the claims and the equivalents thereof.

The Abstract is provided to comply with 37 C.F.R. §1.72(b) is submitted with the understanding that it will not be used to interpret or limit the scope or meaning of the claims.

What is claimed is:

1. A sulfur dioxide sensor comprising:
a first beam having a first functionalized sensing beam surface capable of sensing sulfur dioxide, the first beam capable of producing a first resonant frequency; and
a second beam having a second functionalized reference beam surface not capable of sensing sulfur dioxide, the second beam capable of producing a second resonant frequency, wherein differential sensing of sulfur dioxide may be performed, further wherein the first beam is functionalized with a liquid phase of a first polymeric compound and the second beam is functionalized with a liquid phase of a second polymeric compound.

2. The sensor of claim 1 wherein the functionalized sensing surface and the functionalized reference surface are each ultra thin.

3. The sensor of claim 2 wherein the first polymeric compound is selected from poly(2-vinylpyridine), poly(4-vinylpyridine), poly(4-vinylpyridine-co butylmethacrylate), and combinations thereof.

4. The sensor of claim 3 wherein the second polymeric compound is polystyrene.

5. The sensor of claim 1 comprising a nano sensor capable of performing differential sensing by monitoring changes in the resonant frequency of the first beam relative to the resonant frequency of the second beam.

6. The sensor of claim 5 wherein the first beam and the second beam are located on a single silicon substrate.

7. The sensor of claim 1 wherein the first beam and the second beam are located on different silicon substrates.

8. The sensor of claim 7 comprising a low drift sensor capable of detecting sulfur dioxide levels up to a zeptogram level.

9. The sulfur dioxide sensor of claim 7, further comprising:
- a first frequency measuring circuit for measuring the resonant frequency of the first beam;
- a second frequency measuring circuit for measuring the resonant frequency of the second beam; and
- a control for analyzing the signals from the first frequency measuring circuit and the second frequency measuring circuit, wherein a differential frequency equivalent to the first frequency minus the second frequency is determinable, wherein differential sensing of sulfur dioxide exposure is performed.

10. A method of forming a sulfur dioxide sensor comprising:
- functionalizing a first silicon beam surface with a liquid phase of a first polymeric compound to obtain an ultra thin film capable of detecting sulfur dioxide; and
- functionalizing a second silicon beam surface with a liquid phase of a second polymeric compound to obtain an ultra thin film capable of preventing detection of sulfur dioxide.

11. The method of claim 10 wherein the liquid phase of the first polymeric compound is obtained by dissolution in pyridine.

12. The method of claim 10 wherein the liquid phase of the second polymeric compound is obtained by dissolution in ethanol.

13. The method of claim 10 wherein the first polymeric compound is selected from poly(2-vinylpyridine), poly(4-vinylpyridine), poly(4-vinylpyridine-co butylmethacrylate), and combinations thereof.

14. The method of claim 10 wherein the second polymeric compound is polystyrene.

15. The method of claim 10 further comprising:
- connecting frequency measuring circuits to the silicon surface to produce differential resonant frequency changes;
- connecting a mixer to the frequency measuring circuits to measure the differential resonant frequency changes; and
- outputting the differential resonant frequency changes to a presentation device.

16. The method of claim 10 wherein the silicon surface is a silicon wafer.

17. A method of detecting sulfur dioxide comprising:
- exposing first and second beams to sulfur dioxide, wherein the first beam has a functionalized surface to detect sulfur dioxide and the second beam has a functionalized surface to prevent detection of sulfur dioxide; and
- comparing the resonant frequency of the first beam to the resonant frequency of second beam, wherein an amount of carbon sulfur dioxide exposure is determined.

18. The method of claim 17 wherein the first and second beams are nano-beams.

19. A system comprising:
- a sulfur dioxide sensor comprising
  - a first beam having a first functionalized sensing beam surface capable of sensing sulfur dioxide, the first beam capable of producing a first resonant frequency; and
  - a second beam having a second functionalized reference beam surface not capable of sensing sulfur dioxide, the second beam capable of producing a second resonant frequency, wherein differential sensing of sulfur dioxide may be performed, further wherein the first beam is functionalized with a liquid phase of a first polymeric compound and the second beam is functionalized with a liquid phase of a second polymeric compound;
- a first frequency measuring circuit for measuring the resonant frequency of the first beam;
- a second frequency measuring circuit for measuring the resonant frequency of the second beam; and
- a control for analyzing the signals from the first frequency measuring circuit and the second frequency measuring circuit, wherein a differential frequency equivalent to the first frequency minus the second frequency is determinable, wherein differential sensing of sulfur dioxide exposure is performed.

20. The system of claim 19 wherein the first beam and the second beam are located on different silicon substrates.

* * * * *